United States Patent [19]

Senn-Bilfinger

[11] Patent Number: 4,472,409

[45] Date of Patent: Sep. 18, 1984

[54] 2-PYRIDYLMETHYL THIO(SULFINYL)BENZIMIDAZOLES WITH GASTRIC ACID SECRETION INHIBITING EFFECTS

[75] Inventor: Jörg Senn-Bilfinger, Constance, Fed. Rep. of Germany

[73] Assignee: Byk Gulden Lomberg Chemische Fabrik Gesellschaft mit beschränkter Haftung, Constance, Fed. Rep. of Germany

[21] Appl. No.: 437,883

[22] Filed: Oct. 29, 1982

[30] Foreign Application Priority Data

Nov. 5, 1981 [CH] Switzerland .......................... 7080/81
Nov. 5, 1981 [CH] Switzerland .......................... 7081/81

[51] Int. Cl.³ ..................... A61K 31/44; C07D 235/12
[52] U.S. Cl. ...................................... 424/263; 546/271
[58] Field of Search .......................... 546/271; 424/263

[56] References Cited

U.S. PATENT DOCUMENTS

| 4,045,563 | 8/1977 | Berntsson | 424/263 |
| 4,045,564 | 8/1977 | Berntsson | 424/263 |
| 4,255,431 | 3/1981 | Junggren | 424/263 |
| 4,359,465 | 11/1982 | Ruwart | 424/234 |

FOREIGN PATENT DOCUMENTS

| 0074341 | 3/1983 | European Pat. Off. |
| 7534910 | 6/1977 | France |
| 2392021 | 12/1978 | France |

Primary Examiner—Jane T. Fan
Attorney, Agent, or Firm—Berman, Aisenberg & Platt

[57] ABSTRACT 4- or 5-Trifluoromethyl-2-[(4-methoxy-2-pyridylmethyl)thio or sulfinyl]-(1H)-benzimidazoles are useful as such or in medicament compositions for protecting the stomach and intestines and for inhibiting gastric acid secretion of warm-blooded animals to which they are administered.

23 Claims, No Drawings

2-PYRIDYLMETHYL THIO(SULFINYL)BENZIMIDAZOLES WITH GASTRIC ACID SECRETION INHIBITING EFFECTS

BACKGROUND

1. Field of the Invention

The invention relates to substituted benzimidazoles, their use, and medicaments containing them.

The compounds according to the invention are used in the pharmaceutical industry as intermediates and for the preparation of medicaments.

2. Prior Art*

German Offenlegungsschrift DE-OS No. 1,804,450 (=British Pat. No. 1,234,058) concerns benzazole derivatives which are said to have a tuberculostatic, insecticidal, fungicidal, antiviral, anthelmintic and anti-inflammatory action. DE-OS No. 2,504,252 (=U.S. Pat. No. 4,045,564) claims 2-benzimidazolyl 2-pyridyl sulfides, some of which are said to have an inhibiting effect on secretion of hydrochloric acid in the stomach, and some of which are said to have a stimulating effect on secretion of hydrochloric acid in the stomach. DE-OS No. 2,548,340 (=U.S. Pat. No. 4,045,563) refers to 2-benzimidazolyl 2-pyridyl sulfoxides, which are said to inhibit exogenically or endogenically stimulated secretion of hydrochloric acid in the stomach. European Patent Specification EP-B1 No. 0,005,129 (=U.S. Pat. No. 4,255,431 and U.S. Pat. No. 4,337,257) considers 2-benzimidazolyl 2-pyridyl sulfoxides, which are said to be used in pharmaceutical products for inhibiting secretion of hydrochloric acid in the stomach. The corresponding substituted sulfides, which can be used for the preparation of the previously-mentioned sulfoxides, are mentioned in DE-OS No. 2,548,340 and in EP-B1 No. 0,005,129 exclusively as intermediates, without indication of pharmacological activity. European Patent Application EP-A1 No. 0,045,200 deals with substituted heterocyclylalkylsulfinylbenzimidazoles, which are said to be used in the treatment or prevention of special gastrointestinal inflammatory diseases.

*The equivalent English-language patents were located with the aid of the "Patent No. Family Index" from Inpadoc.

SUMMARY OF THE INVENTION

It has now been found, surprisingly, that the 2-benzimidazolyl 2-pyridylmethyl sulfides and sulfoxides according to the invention, which are hereinafter described in more detail, have interesting and unexpected properties which advantageously distinguish them from known compounds.

The invention relates to new substituted benzimidazoles, all of which concurrently bear a trifluoromethyl substituent on a benzene (of the benzimidazole) ring and a methoxy substituent on a pyridine ring. These benzimidazoles are compounds of the formula

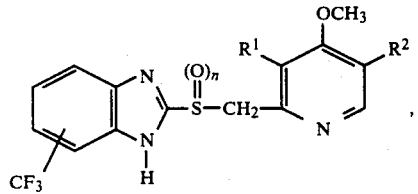

(I)

wherein $R^1$ denotes hydrogen or methyl,
$R^2$ denotes hydrogen or methyl and
n denotes the numbers of 0 or 1,
and salts of these compounds.

Among the contemplated salts of compounds of formula I, wherein n denotes 0 (sulfides), are all of the acid-addition salts. The pharmacologically-acceptable salts of the inorganic and organic acids usually employed galenically are notable examples. Pharmacologically-unacceptable salts, which may be obtained initially as process products, for example in the preparation of compounds according to the invention on an industrial scale, are converted into pharmacologically-acceptable salts by conventional processes which are known to the artisan. All acid-addition salts of compounds of formula I which are not pharmacologically acceptable are conventionally converted into either the corresponding free base or into a pharmacologically-acceptable acid-addition salt. Examples of suitable pharmacologically-acceptable salts are water-soluble and water-insoluble acid-addition salts, such as the hydrochloride, hydrobromide, hydroiodide, phosphate, nitrate, sulfate, acetate, citrate, gluconate, benzoate, hibenzate [2-(4-hydroxybenzoyl)benzoate], fendizoate (o-[(2'-hydroxy-4-biphenylyl)carbonyl]benzoate), butyrate, sulfosalicylate, maleate, laurate, malate, fumarate, succinate, oxalate, tartrate, amsonate (4,4'-diaminostilbene-2,2'-disulfonate), embonate [4,4'-methylene-bis-(3-hydroxy-2-naphthoate)], metembonate [4,4'-methylene-bis-(3-methoxy-2-naphthoate)], stearate, tosylate (p-toluenesulfonate), 2-hydroxy-3-naphthoate, 3-hydroxy-2-naphthoate and mesylate (methanesulfonate).

Compounds of formula I, wherein n denotes 1 (sulfoxides) are also convertible into the previously-noted acid-addition salts. These salts, however, do not have the same stability (in aqueous solution) as corresponding salts of the sulfides. On the other hand, the sulfoxides are convertible into their basic salts by reaction with appropriate deprotonization agents, such as inorganic and organic bases. These basic salts are also within the scope of the invention. All basic salts of compounds of formula I which are not pharmacologically acceptable are conventionally converted into either the corresponding free compound or into a pharmacologically-acceptable basic salt.

Substituted benzimidazoles of the formula

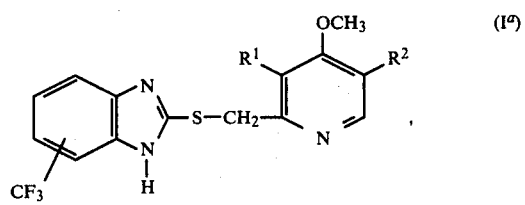

(I<sup>a</sup>)

wherein $R^1$ and $R^2$ have their previously-ascribed meanings, and salts of these compounds, form an embodiment of the invention.

Substituted benzimidazoles of the formula

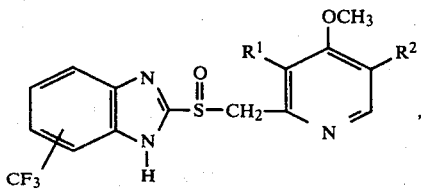

wherein $R^1$ and $R^2$ have their previously-ascribed meanings, and salts of these compounds,
form another embodiment of the invention.

Illustrative compounds according to the invention are: 4-trifluoromethyl-2-[(4-methoxy-2-pyridylmethyl)-thio]-(1H)-benzimidazole, 4-trifluoromethyl-2-[(4-methoxy-3-methyl-2-pyridylmethyl)thio]-(1H)-benzimidazole, 4-trifluoromethyl-2-[(4-methoxy-5-methyl-2-pyridylmethyl)thio]-(1H)-benzimidazole, 4-trifluoromethyl-2-[(4-methoxy-3,5-dimethyl-2-pyridylmethyl)thio]-(1H)-benzimidazole, 5-trifluoromethyl-2-[(4-methoxy-2-pyridylmethyl)thio]-(1H)-benzimidazole, 5-trifluoromethyl-2-[(4-methoxy-3-methyl-2-pyridylmethyl)thio]-(1H)-benzimidazole, 5-trifluoromethyl-2-[(4-methoxy-5-methyl-2-pyridylmethyl)thio]-(1H)-benzimidazole and 5-trifluoromethyl-2-[(4-methoxy-3,5-dimethyl-2-pyridylmethyl)thio]-(1H)-benzimidazole, 4-trifluoromethyl-2-[(4-methoxy-2-pyridylmethyl)-sulfinyl]-(1H)-benzimidazole, 4-trifluoromethyl-2-[(4-methoxy-3-methyl-2-pyridylmethyl)sulfinyl]-(1H)-benzimidazole, 4-trifluoromethyl-2-[(4-methoxy-5-methyl-2-pyridylmethyl)sulfinyl]-(1H)-benzimidazole, 4-trifluoromethyl-2-[(4-methoxy-3,5-dimethyl-2-pyridylmethyl)sulfinyl]-(1H)-benzimidazole, 5-trifluoromethyl-2-[(4-methoxy-2-pyridylmethyl)sulfinyl]-(1H)-benzimidazole, 5-trifluoromethyl-2-[(4-methoxy-3-methyl-2-pyridylmethyl)sulfinyl]-(1H)-benzimidazole, 5-trifluoromethyl-2-[(4-methoxy-5-methyl-2-pyridylmethyl)sulfinyl]-(1H)-benzimidazole and 5-trifluoromethyl-2-[(4-methoxy-3,5-dimethyl-2-pyridylmethyl)sulfinyl]-(1H)-benzimidazole, and their salts.

Particularly preferred compounds are 5-trifluoromethyl-2-[(4-methoxy-3-methyl-2-pyridylmethyl)thio]-(1H)-benzimidazole, 5-trifluoromethyl-2-[(4-methoxy-3,5-dimethyl-2-pyridylmethyl)sulfinyl]-(1H)-benzimidazole and 5-trifluoromethyl-2-[(4-methoxy-2-pyridylmethyl)sulfinyl]-(1H)-benzimidazole and their pharmacologically-acceptable salts.

Because of tautomerism in the imidazole ring, 4- and 5-substitution in the benzimidazole is identical to 7- and, respectively, 6-substitution.

The invention furthermore relates to a process for the preparation of the substituted benzimidazoles of formula I, wherein $R^1$, $R^2$ and n have the previously-ascribed meanings, and of their salts.

The process is characterized by reacting:

(a) a mercaptobenzimidazole of formula II with a picoline derivative III

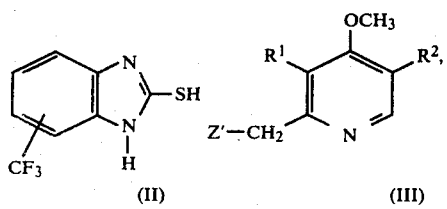

(b) a benzimidazole of formula IV with a mercaptopicoline V

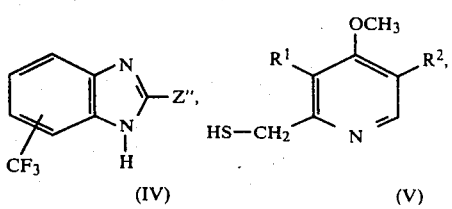

(c) an o-phenylenediamine of formula VI with a formic acid derivative VII

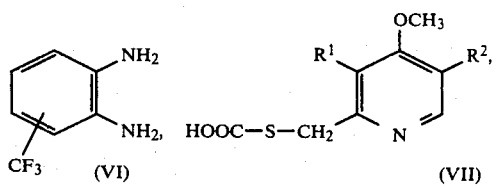

and, if appropriate, the 2-benzimidazolyl 2-pyridyl sulfides of formula VIII

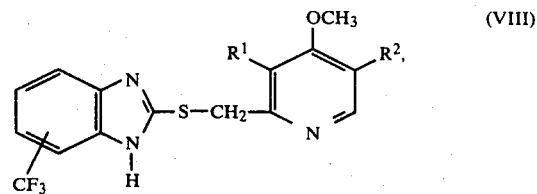

obtained according to (a), (b), or (c) are then oxidized and/or converted into salts, or (d) a benzimidazole of formula IX with a pyridine derivative X

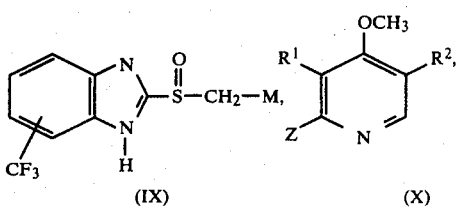

(e) a sulfinyl compound of formula XI with a 2-picoline derivative of formula XII

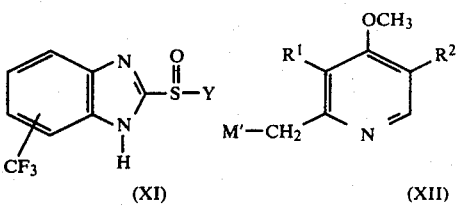

and, if appropriate, the products are then converted into salts, Y, Z, Z' and Z" being suitable leaving groups, M representing an alkali metal atom (Li, Na or K), M' representing the equivalent of a metal atom and $R^1$, $R^2$ and n having their previously-mentioned meanings.

The processes (a), (b) and (c) lead to sulfides according to the invention, the oxidation of compounds VIII and the processes (d) and (e) lead to the sulfoxides according to the invention.

The expert, on the basis of his expert knowledge, is familiar with which leaving groups Y, Z, Z' and Z" are suitable. A suitable leaving group Y is, for example, a group which, together with the sulfinyl group to which it is bonded, forms a reactive sulfinic acid derivative. A suitable leaving group Y is, for example, an alkoxy group, a dialkylamino group or an alkylmercapto group. Examples of suitable leaving groups Z, Z' and Z" are halogen atoms, in particular chlorine atoms, or hydroxyl groups activated by esterification (for example with p-toluenesulfonic acid). The equivalent of a metal atom M' is an alkali metal atom (Li, Na or K), or an alkaline earth metal atom (e.g. Mg) which is substituted by a halogen atom (e.g. Br, Grignard reagent), or any other optionally substituted metal atom which is known to react in substitution reactions of organometallic compounds in the same manner as the abovementioned metal atoms.

The reaction of II with III is carried out in a manner which is known per se in suitable, preferably polar, solvent (such as methanol, dimethylsulfoxide, acetone, dimethylformamide or acetonitrile) with the addition or exclusion of water. It is carried out, for example, in contact with a proton acceptor. Examples of suitable proton acceptors are alkali-metal hydroxides, such as sodium hydroxide; alkali-metal carbonates, such as potassium carbonate; and tertiary amines, such as pyridine, triethylamine or ethyl diisopropylamine. Alternatively, the reaction is carried out without a proton acceptor, whereby—depending on the starting compounds—an acid-addition salt is optionally obtained in the first place. The reaction temperature is, e.g., between 0° and 150° C., temperatures between 50° C. and 100° C., especially the boiling point of the solvent used, being preferred.

Similar reaction conditions to those in the reaction of II with III are used in the reaction of IV with V, which is carried out in a manner which is known per se.

The reaction of VI with VII is preferably carried out in polar, optionally water-containing, solvent in the presence of a strong acid, for example hydrochloric acid, in particular at the boiling point of the solvent used.

The oxidation of sulfide VIII is carried out in a manner which is known per se and under conditions with which an expert is familiar for oxidation of sulfides to give sulfoxides [cf. J. Drabowicz and M. Mikolajczyk, Organic preparations and procedures int. 14(1-2), 45–89 (1982)]. Illustrative oxidizing agents are all reagents usually employed for oxidation of sulfides, in particular peroxyacids, such as peroxyacetic acid, trifluoroperoxyacetic acid, 3,5-dinitroperoxybenzoic acid, peroxymaleic acid or, preferably, m-chloroperoxybenzoic acid. The reaction is expediently conducted in inert solvent, for example aromatic or chlorinated hydrocarbon, such as benzene, toluene, methylene chloride or chloroform. The reaction temperature is between −70° C. and the boiling point of the solvent used, but preferably between −30° C. and +20° C. (depending on the reactivity of the oxidizing agent and the degree of dilution). The oxidation with halogen or hypohalogenite (e.g. with aqueous sodium hypochlorite solution), which is carried out expediently at temperatures between 0° and 30° C. is very advantageous.

The reaction of IX with X is preferably carried out in inert solvent, such as one which is also usually employed for the reaction of enolate ions with alkylating agents. Examples include aromatic solvents, such as benzene or toluene. The reaction temperature is as a rule between 0° and 120° C. (depending on the nature of the alkali-metal atom M and the leaving group Z), preferably at the boiling point of the solvent. For example [if M represents Li (lithium), Z represents Cl (chlorine) and the reaction is carried out in benzene], the boiling point of benzene (80° C.) is preferred. The compounds XI are reacted with compounds XII in a manner which is known per se and under conditions with which the expert is familiar for the reaction of organometallic compounds.

The compounds according to the invention are initially obtained either as such as as their salts, depending on the nature of the starting compounds and depending on the reaction conditions.

Moreover, salts are obtained by dissolving the free compounds in a suitable solvent, for example in a chlorinated hydrocarbon, such as methylene chloride or chloroform, or a low-molecular aliphatic alcohol (ethanol or isopropanol), which contains the desired acid or base or to which the desired acid or base is subsequently added, if necessary in the precisely calculated stoichiometric amount.

The salts are isolated by filtration, reprecipitation or precipitation or by evaporation of the solvent.

Resulting salts are converted into the free compounds by treatment with bases or acids, for example with aqueous sodium bicarbonate or with dilute hydrochloric acid, and the free compounds are optionally conventionally converted into their salts. By this means, the compounds are purified, or pharmacologically-unacceptable salts are converted into pharmacologically-acceptable salts.

The sulfoxides according to the invention are optically active compounds. The invention thus includes both the enantiomers and their mixture and racemates. The enantiomers can be separated in a manner which is known to the expert, e.g. by preparation and separation of corresponding diastereoisomers. The enantiomers can also be prepared by asymmetric synthesis, e.g. by reaction of pure optically active or diastereoisomerically pure compounds XI with compounds XII [cf. K. K. Andersen, Tetrahedron Lett., 93 (1962)].

The compounds according to the invention are preferably synthesized by reaction of compounds II with III and optionally subsequent oxidation of the resulting sulfides VIII.

The compounds of the formulae II–VII and IX–XII are either known, or they are prepared by processes analogous to known processes from available starting materials. Thus, for example, compounds II are obtained by reacting compounds VI [E. Pouterman and A. Girardet, Helvet. Chim. Acta 30, 107 (1947)] with carbon disulfide. Compounds III are prepared, e.g., according to O. E. Schulz and S. Fedders, Arch. Pharm. (Weinheim) 310, 128–136 (1977).

The compounds IX are prepared, for example, from the compounds II by methylation, oxidation and subsequent deprotonization with alkali metal hydrides or alkanolates or customary organometallic compounds. The compounds X are prepared according to Z. Talik, Roczniki Chem. 35, 475 (1961).

EXAMPLES

The examples which follow illustrate the invention in more detail, without restricting it. m.p. denotes melting point, b.p. denotes boiling point. Diethyl ether is referred to merely as "ether".

1.
4-Trifluoromethyl-2-[(4-methoxy-2-pyridylmethyl)sulfinyl]-(1H)-benzimidazole 2.3 g of commercially available 85% strength m-chloroperoxybenzoic acid, dissolved in 30 ml of methylene chloride, are added dropwise to a solution, cooled to −30° C., of 3.0 g (0.0088 mole) of 4-trifluoromethyl-2-[(4-methoxy-2-pyridylmethyl)thio]-(1H)-benzimidazole in 50 ml of methylene chloride over the course of 45 minutes. The resulting mixture is then stirred for a further 60 minutes, and the temperature is subsequently allowed to rise to 0° C. After the mixture is washed with saturated aqueous sodium carbonate solution (30 ml), it is dried over sodium sulfate, and the solvent is stripped off in vacuo. The solid residue which remains is recrystallized successively from isopropanol and acetonitrile. Yield: 1.6 g of title compound, m.p. 150° to 151° C.

2.
5-Trifluoromethyl-2-[(4-methoxy-2-pyridylmethyl)sulfinyl]-(1H)-benzimidazole 0.1 g of the title compound of m.p. 166° C. (with decomposition, recrystallized twice from isopropanol) is obtained, by a method analogous to that in Example 1, starting from 0.3 g (0.92 mole) of 5-trifluoromethyl-2-[(4-methoxy-2-pyridylmethyl)thio]-(1H)-benzimidazole and 0.3 g of 85% strength m-chloroperoxybenzoic acid.

3.
5-Trifluoromethyl-2-[(4-methoxy-3-methyl-2-pridylmethyl)sulfinyl]-(1H)-benzimidazole 2.9 g of the title compound of m.p. 225° to 227° C. (with decomposition, from toluene/ether) are obtained, by a method analogous to that in Example 1, from 3.7 g (0.01 mole) of 5-trifluoromethyl-2-[(4-methoxy-3-methyl-2-pyridylmethyl)thio]-(1H)-benzimidazole and 3.3 g of 85% strength m-chloroperoxy-benzoic acid.

4.
5-Trifluoromethyl-2-[(4-methoxy-3,5-dimethyl-2-pyridylmethyl)sulfinyl]-(1H)-benzimidazole 3.1 g of the title compound of m.p. 163° C. (from acetonitrile) are obtained, by a method analogous to that in Example 1, starting from 3.8 g (0.01 mole) of 5-trifluoromethyl-2-[(4-methoxy-3,5-dimethyl-2-pyridylmethyl)thio]-(1H)-benzimidazole and 3.5 g of 85% strength m-chloroperoxybenzoic acid.

5.
4-Trifluoromethyl-2-[(4-methoxy-2-pyridylmethyl)thio]-(1H)-benzimidazole 4.5 g (0.023 mole) of 2-chloromethyl-4-methoxypyridine hydrochloride are added to 5.0 g (0.023 mole) of 4-trifluoromethyl-2-mercaptobenzimidazole, dissolved in 100 ml of ethanol and 23 ml of 2N sodium hydroxide solution, and the obtained mixture is stirred at room temperature for 6 hours. After most of the solvent is stripped off, the residue is extracted with three 50 ml portions of ethyl acetate, the extract is washed with distilled water and dried over sodium sulfate and the solvent is stripped off in vacuo. The solid residue is recrystallized from acetonitrile. Yield: 5.9 g (76%) of title compound, m.p. 146° C.,

6.
5-Trifluoromethyl-2-[(4-methoxy-2-pyridylmethylthio]-(1H)-benzimidazole 2.7 g (59%) of the title compound of m.p. 180° to 182° C. (from acetonitrile) are obtained, by a method analogous to that of Example 5, from 3.0 g (0.014 mole) of 5-trifluoromethyl-2-mercaptobenzimidazole and 2.7 g of 2-chloromethyl-4-methoxypyridine hydrochloride, after boiling under reflux for three hours.

7.
5-Trifluoromethyl-2-[(4-methoxy-3-methyl-2-pyridylmethyl)thio]-(1H)-benzimidazole 2.9 g of the title compound of m.p. 148° C. (from acetonitrile) are obtained, by a method analogous to that in Example 5, from 2.2 g (0.01 mole) of 5-trifluoromethyl-2-mercaptobenzimidazole and 2.1 g of 2-chloromethyl-4-methoxy-3-methylpyridine hydrochloride.

8.
5-Trifluoromethyl-2-[(4-methoxy-3,5-dimethyl-2-pyridylmethyl)thio]-(1H)-benzimidazole 3.5 g of the title compound of m.p. 163° C. (from acetonitrile) are obtained, by a method analogous to that in Example 5, from 2.2 g of 5-trifluoromethyl-2-mercaptobenzimidazole and 2.2 g of 2-chloromethyl-4-methoxy-3,5-dimethylpyridine hydrochloride.

9.
4-Trifluoromethyl-2-[(4-methoxy-3-methyl-2-pyridylmethyl)thio]-(1H)-benzimidazole 3.1 g of the title compound of m.p. 175° C. (from isopropanol/ether) are obtained, by a method analogous to that in Example 5, from 2.2 g (0.01 mole) of 4-trifluoromethyl-2-mercaptobenzimidazole and 2.1 g of 2-chloromethyl-4-methoxy-3-methylpyridine hydrochloride.

10. 4-Trifluoromethyl-2-mercaptobenzimidzole 4.4 g of solid potassium hydroxide, dissolved in 14 ml of water, and 6 g (0.08 mole) of carbon disulfide are added successively to a solution of 11.0 g (0.062 mole) of 3-trifluoromethyl-o-phenylenediamine in 100 ml of ethanol. The mixture is heated under reflux (bath temperature of 60° C.) for 4 hours with stirring. After the mixture has been cooled to 10° C., the precipitate which has separated out is filtered off with suction and recrystallized from isopropanol to obtain 13.0 g (96%) of the title compound, m.p. 315° to 320° C.

5-Trifluoromethyl-2-mercaptobenzimidazole is obtained in an analogous manner from 4-trifluoromethyl-o-phenylene-diamine and carbon disulfide (m.p. 308° to 310° C.).

11. 2-Chloromethyl-4-methoxypyridine hydrochloride 15 ml of thionyl chloride are added dropwise to a solution, cooled to −10° C., of 10 g (0.072 mole) of 2-hydroxymethyl-4-methoxypyridine in 30 ml of dry chloroform over the course of 15 minutes. The solution is allowed to come to room temperature and is stirred for another one and a half hours. After the solvent and the excess thionyl chloride have been stripped off, colorless crystals are obtained and are recrystallized from isopropanol to yield the title compound [12.1 g (87%), m.p. 140° to 141° C., decomposition).

2-Chloromethyl-4-methoxy-3-methylpyridine hydrochloride (m.p. 151° to 153° C., from isopropanol/ether) and 2-chloromethyl-4-methoxy-3,5-dimethylpyridine hydrochloride (m.p. 128° C., from isopropanol/ether) are obtained in an analogous manner by reacting 2-hydroxymethyl-4-methoxy-3-methylpyridine or, respectively, 2-hydroxymethyl-4-methoxy-3,5-dimethylpyridine with thionyl chloride.

The compounds 2-hydroxymethyl-4-methoxypyridine and 2-hydroxymethyl-4-methoxy-3-methylpyridine are prepared according to O. E. Schulz and S. Fedders, Arch. Pharm. (Weinheim) 310, 128 (1977). The starting compound 2,3-dimethyl-4-nitropyridine-N-oxide is prepared according to H. C. Brown, S. Johnson and H. Podall, J. Am. Chem. Soc. 76, 5556 (1954).

12. 2-Hydroxymethyl-4-methoxy-3,5-dimethylpyridine hydrochloride 18 g of 2,3,5-trimethylpyridine [F. Bohlmann, A. Englisch, J. Politt, H. Sander and W. Weise, Chem.Ber. 88, 1831 (1955)] and 17 ml of 30% strength hydrogen peroxide are heated in 80 ml of glacial acetic acid for 2.5 hours at 100° C. After this time additional 10 ml of 30% strength hydrogen peroxide are added and the mixture is kept at 100° C. for a further 8 hours. The mixture is then concentrated to half of its volume in vacuo. If the solution is free of peroxide, the remaining solvent is stripped off in vacuo. The residue is distilled under a high vacuo. 19.2 g (95%) of 2,3,5-trimethylpyridine-N-oxide of b.p. 95°–98° C. (1.3 Pa) are obtained.

5.0 g of this compound are dissolved at room temperature in 7 ml of fuming nitric acid and 7 ml of concentrated sulphuric acid. This mixture is heated for 18 hours at 40° C. and is then poured onto ice water. It is made alkaline by addition of concentrated sodium hydroxide solution with cooling. The mixture is extracted with ethyl acetate and the organic phase is concentrated in vacuo. The resulting crude 2,3,5-trimethyl-4-nitropyridine-N-oxide is dissolved without further purification in 20 ml of dry methanol. 4.7 ml of 30% strength sodium methoxide solution are added, and the mixture is heated for 12 hours at 50° C. The solvent is then removed. The residue is dissolved in water and extracted with ethyl acetate. The organic phase is concentrated and the resulting oil (crude 4-methoxy-2,3,5-trimethylpyridine-N-oxide) is poured into 20 ml of hot (100° C.) acetic anhydride. The mixture is kept for one hour at this temperature. It is then concentrated in vacuo and dissolved without further purification in 20 ml of 10% strength aqueous hydrochloric acid. The solution is stirred for 2.5 hours at 50° C. and is then concentrated to half of its volume in vacuo. The remaining solution is made alkaline with potassium carbonate and is extracted with ethyl acetate. The organic phase is dried with sodium sulphate and concentrated in vacuo. The oily residue is dissolved in 50 ml of ethyl methyl ketone. An etheral solution of hydrogen chloride is added to precipitate the title compound quantitatively. The precipitate is recrystallized from dioxan/isopropanol. 3.1 g of the title compound of m.p. 126° C. are obtained.

13. 5-Trifluoromethyl-2-[(4-methoxy-2-pyridylmethyl)thio]-(1H)-benzimidazole A hot solution of 2.06 g (10.6 mmol) of 2-chloromethyl-4-methoxypyridine hydrochloride in 20 ml of isopropanol is added to a solution of 2.25 g (10.3 mmol) of 5-trifluoromethyl-2-mercaptobenzimidazole in 19 ml of isopropanol, and the mixture is stirred at 100° C. for 4 hours. After cooling in an ice-bath 4.21 g (99%) of 5-trifluoromethyl-2-[(4-methoxy-2-pyridylmethyl)thio]-(1H)-benzimidazole dihydrochloride of m.p. 195°–197° C. (decomposition) are obtained.

A solution of 4.66 g (11.3 mmole) of the dihydrochloride in 13 ml of water is purified with active charcoal. 3.7 g (96%) of the free base are precipitated by slow addition of 17 ml of a 2N. potassium bicarbonate solution, which contains a little isopropanol. M.p. 182°–184° C.

14. 5-Trifluoromethyl-2-[(4-methoxy-2-pyridylmethyl)sulfinyl]-(1H)-benzimidazole 600 ml of a 1.5% strength aqueous sodium hypochlorite solution are added within 3 minutes at 10° C. with vigorous stirring to a solution of 16.2 g (0.048 mole) of 5-trifluoromethyl-2-[(4-methoxy-2-pyridylmethyl)thio]-(1H)-benzimidazole in 960 ml of ethyl acetate. The mixture is then stirred for a further 2 minutes. The organic phase is separated off and is washed with 100 ml of distilled water. The aqueous phase is adjusted to pH 7–8 by addition of glacial acetic acid and is then extracted three times with ethyl acetate. The extracts are washed with water and the combined organic phases are then concentrated to a volume of 100 ml and cooled in an ice bath. The precipitate which has separated out is filtered off with suction and washed with cold ethyl acetate. Yield: 13.2 g of m.p. 166° C. (decomposition).

15. 5-Trifluoromethyl-2-[(4-methoxy-2-pyridylmethyl)sulfinyl]-(1H)-benzimidazole A suspension of 20.0 g (0.092 mole) of 5-trifluoromethyl-2-mercaptobenzimidazole and 13.1 g (0.092 mole) of methyl iodide in 200 ml of ethanol is heated to the boil for three hours. The solvent is stripped off in vacuo and the residue is recrystallized from acetonitrile. 17.5 g (82%) of 5-trifluoromethyl-2-methylthio-benzimidazole of m.p. 145°–146° C. are obtained.

2.6 g (0.013 mole) of commercially available 85% strength m-chloroperoxybenzoic acid are added dropwise to a suspension, cooled to −20° C., of 3.0 g (0.013 mole) of 5-trifluoromethyl-2-methylthio-benzimidazole in 50 ml of methylene chloride in the course of 30 minutes. The mixture is then stirred for a further 60 minutes and is then extracted twice with, each time, 20 ml of an aqueous potassium carbonate solution. The solvent is stripped off in vacuo and the solid residue which remains is recrystallized from acetonitrile. 1.8 g of 5-trifluoromethyl-2-methylsulfinyl-benzimidazole of m.p. 135° C. are obtained. Deprotonation of this compound with n-butyllithium and reaction with 2-chloro-4-methoxypyridine in dry benzene yields the title compound of m.p. 166° C. (decomposition).

16. 5-Trifluoromethyl-2-[(4-methoxy-3,5-dimethyl-2-pyridylmethyl)thio]-(1H)-benzimidazole 2.27 g of 2-[2-(4-methoxy-3,5-dimethyl-2-pyridylmethyl)thio]formic acid and 1.76 g of 4-trifluoromethyl-o-phenylenediamine are heated under reflux for two hours in 20 ml of 4N. hydrochloric acid. The mixture is cooled and neutralized with ammonia solution. The neutral solution is then extracted with ethyl acetate.

The solvent is stripped off in vacuo and the solid residue which remains is recrystallized from acetonitrile. M.p. 163° C.

17.
5-Trifluoromethyl-2-[(4-methoxy-2-pyridylmethyl)thio]-(1H)-benzimidazole 22.1 g (0.1 mole) of 5-trifluoromethyl-2-chlorobenzimidazole and 15.7 g (0.11 mole) of 4-methoxy-2-thiomethylpyridine in 250 ml of isopropanol are heated under reflux for 10 hours. The solvent is stripped off in vacuo, and 500 ml of ice water are added to the residue. The title compound is filtered off with suction and recrystallized from acetonitrile. M.p. 180°–182° C.

18.
5-Trifluoromethyl-2-[(4-methoxy-2-pyridylmethyl)sulfinyl]-(1H)-benzimidazole calcium salt 0.09 g (0.003 mole) of 80% sodium hydride (in paraffin) are added to a solution of 1.1 g of 5-trifluoromethyl-2-[(4-methoxy-2-pyridylmethyl)-sulfinyl]-(1H)-benzimidazole in 20 ml of dry dioxan under an inert gas atmosphere. After the evolution of gas has subsided, the solvent is stripped off in vacuo. The residue (5-trifluoromethyl-2-[(4-methoxy-2-pyridylmethyl)-sulfinyl]-(1H)-benzimidazole sodium salt) is dissolved in a little water, and a 1% strength aqueous calcium chloride solution is added. The precipitate which has separated out is filtered off with suction and dried in a high-vacuum for several hours. M.p. 176° C. (decomposition).

COMMERCIAL USEFULNESS

The substituted benzimidazoles of formula I and their pharmacologically-acceptable salts have valuable pharmacological properties which render them commercially useful. In particular, they significantly inhibit gastric acid secretion. In addition, they are characterized by an excellent protective action on the stomach and intestines of warm-blooded animals. The term "protective action on the stomach and intestines" comprises the prevention and treatment of non-cancerous gastrointestinal diseases, especially gastrointestinal inflammatory diseases and lesions (such as, for example, gastric ulcer, duodenal ulcer, gastritis) which are caused, e.g., by microorganisms, bacterial toxins, medicaments (such as certain antiphlogistics and antirheumatics), other chemicals (such as ethanol), gastric acid or stress situations.

This protective action can even be observed on administering doses which are lower than those needed to inhibit gastric acid secretion. Another advantage of the compounds according to the invention is their comparatively great chemical stability.

The excellent activity of the substituted benzimidazoles and of their pharmacologically-acceptable salts, their low toxicity and the absence of significant side effects enables the subject compounds to be used in human medicine and in veterinary medicine, where they are employed, in particular, for the treatment and prophylaxis of illnesses which are based on diseases of the stomach and intestine and on excessive secretion of gastric acid. For example, acute and chronic ulcus ventriculi and ulcus duodeni, gastritis, hyperacid gastric irritation and stomach complaints caused by medicaments are treated in humans and animals with these compounds or with medicament compositions containing these compounds.

The invention thus also relates to a method of treating mammals suffering from one of the noted illnesses. The method is characterized by administering a therapeutically-active and pharmacologically-acceptable amount of one or more of the specified substituted benzimidazoles to the sick mammal.

The invention furthermore relates to the compounds according to the invention which are used in this method. The invention also relates to the use of compounds according to the invention in the production of medicaments which are useful for combating the illnesses mentioned.

The invention moreover relates to medicaments which contain one or more substituted benzimidazoles of formula I and/or their pharmacologically-acceptable salts.

The medicaments are produced by processes which are known per se and with which an expert is familiar. As medicaments, the pharmacologically-active compounds (=active ingredients) according to the invention are used either as such or, preferably, in combination with suitable pharmaceutical auxiliaries, in the form of tablets, dragees, capsules, suppositories, emulsions, suspensions or solutions. When the new pharmaceutical formulations contain pharmaceutical auxiliaries in addition to one or more compounds according to the invention, the content of active compound in the resulting compositions is from 0.1 to 95, preferably from 0.5 to 50 percent by weight of the total.

The expert is familiar, on the basis of his expert knowledge, with the auxiliaries which are suitable for the desired medicament formulations. Besides solvents, gelling agents, suppository bases, tableting auxiliaries and other excipients for active ingredients, it is also contemplated to use, for example, antioxidants, dispersing agents, emulsifiers, antifoaming agents, flavor correctants, preservatives, solubilizing agents and colorants.

The active compounds are, e.g., administered orally or parenterally, oral and intravenous administration being preferred.

In general, it is advantageous in human medicine to administer the active compound or compounds, when these are given orally, in a daily dose of from about 0.01 to about 20 mg/kg of body weight, preferably from 0.05 to 7 and in particular from 0.1 to 2 mg/kg of body weight, if appropriate in the form of several, preferably 1 to 4, individual administrations to achieve the desired result. In the case of parenteral treatment, similar or (especially with intravenous administration of the active compounds) as a rule lower dosages can be used. The optimum dosage and method of administration of the active compounds required in each particular case are easily determined by any expert in accordance with his expert knowledge.

When a compound according to the invention and/or a salt thereof is used for treatment of one of the mentioned illnesses, the pharmaceutical formulation optionally contains one or more pharmacologically-active members of other groups of medicaments, such as antacids, for example aluminum hydroxide or magnesium aluminate; tranquilizers, such as benzodiazepines, for example diazepam; spasmolytic agents, such as bietamiverine and camylofin; anticholinergic agents, such as oxyphencyclimine and phencarbamide; local anesthetics, such as tetracaine and procaine; and in some cases also enzymes, vitamins or aminoacids.

The active compounds are formulated, for example, in the following manner:

(a) Tablets containing 40 mg of active compound 20 kg of 4-trifluoromethyl-2-[(4-methoxy-2-pyridylmethyl)thio]-(1H)-benzimidazole, 40 kg of lactose, 26 kg of corn starch and 3 kg of polyvinylpyrrolidone are moistened with about 20 liters of water, and the mixture is granulated through a sieve of 1.25 mm mesh width. The granules are dried to a relative moisture content of from 50 to 60% in a fluidized bed drier, and 8 kg of sodium carboxymethyl-cellulose, 2 kg of talc and 1 kg of magnesium stearate are then added. The finished granules are pressed to 200 mg tablets 8 mm in diameter.

(b) Capsules with an active compound content of 30 mg 300 g of 5-trifluoromethyl-2-[(4-methoxy-3-methyl-2-pyridylmethyl)thio]-(1H)-benzimidazole, 695 g of microcrystalline cellulose and 5 g of amorphous silicic acid are finely powdered and mixed thoroughly, and the resulting mixture is filled into hard gelatin capsules, size 4.

(c) Capsules with an active compound content of 10 mg 100 g of 5-trifluoromethyl-2-[(4-methoxy-2-pyridylmethyl)sulfinyl]-(1H)-benzimidazole, 895 g of microcrystalline cellulose and 5 g of amorphous silicic acid are finely powdered and mixed thoroughly, and the mixture is filled into hard gelatin capsules, size 4.

(d) Ampoules containing 30 mg of 5-trifluoromethyl-2-[(4-methoxy-3-methyl-2-pyridylmethyl)thio]-(1H)-benzimidazole A suspension of 60 g of 5-trifluoromethyl-2-[(4-methoxy-3-methyl-2-pyridylmethyl)thio]-(1H)-benzimidazole in 9 kg of distilled water is dissolved and adjusted to a pH of 5 by slow addition of about 171 ml of 1N hydrochloric acid. 90 g of sodium chloride and 5 g of sodium disulfite are added, and the mixture is made up to 10 l with distilled water. It is then filtered under sterile conditions and filled into 5 ml ampoules which are sterilized for 20 minutes at 121° C.

(e) Ampoules containing 30 mg of 5-trifluoromethyl-2-[(4-methoxy-2-pyridylmethyl)sulfinyl]-(1H)-benzimidazole 3 g of 5-trifluoromethyl-2-[(4-methoxy-2-pyridylmethyl)sulfinyl]-(1H)-benzimidazole are added with stirring to a solution of 6 g of sodium carbonate in 90 ml of distilled water. The mixture is made up to 100 ml. Of this solution 1 ml in each case is filled in a vial which is subjected to lyophilization.

PHARMACOLOGY

The excellent protection action on the stomach, and the gastric secretion inhibition shown by the substituted benzimidazoles is demonstrated by a test using the Shay rat model. The compounds according to the invention prove to have a protective action on the stomach and a gastric secretion inhibition which are clearly superior to the state of the art.

The substances investigated in the tests are characterized in the table which follows by means of serial numbers which are allocated as follows:

| Serial No. | Name of Compound |
|---|---|
| 1 | Omeprazole*(INN, USP 4,255,431 |
| 2 | 5-Trifluoromethyl-2-[(4-methoxy-2-pyridylmethyl)sulfinyl]-(1H)—benzimidazole |
| 3 | 5-Trifluoromethyl-2-[(4-methoxy-3-methyl-2-pyridylmethyl)sulfinyl]-(1H)—benzimidazole |
| 4 | 5-Trifluoromethyl-2-[(4-methoxy-3,5-dimethyl-2-pyridylmethyl)sulfinyl]-(1H)—benzimidazole |
| 5 | 4-Methyl-2-[(2-pyridylmethyl)thio]-(1H)—benzimidazole (USP 4,045,564) |
| 6 | 5-Trifluoromethyl-2-[(4-methoxy-2-pyridylmethyl)thio]-(1H)—benzimidazole |
| 7 | 5-Trifluoromethyl-2-[(4-methoxy-3-methyl-2-pyridylmethyl)thio]-(1H)—benzimidazole |
| 8 | 4-Trifluoromethyl-2-[(4-methoxy-3-methyl-2-pyridylmethyl)thio]-(1H)—benzimidazole |

*Omeprazole = 5-Methoxy-2-[(4-methoxy-3,5-dimethyl-2-pyridylmethyl)-sulfinyl]-(1H)—benzimidazole The effect of the compounds according to the invention on the formation of gastric ulcers provoked by a pylorus ligature (4 hours, so-called Shay rat) and oral administration of 100 mg/kg acetylsalicylic acid and on the inhibition of gastric secretion in rats during 4 hours is shown in the following table:

| Serial No. | Dose [mg/kg] p.o. | Protective action on the stomach (rat) reduction in the ulcer index (%) | $ED_{25}+$ [mg/kg, p.o.] | $ED_{50}+$ | Gastric Secretion (rat) inhibition in % of HCl-secretion | $ED_{25}+$ [mg/kg, p.o.] | $ED_{50}+$ |
|---|---|---|---|---|---|---|---|
| 1 | 0.1 | +1 | 0.9 | 2.3 | 5 | ≳3.0 | — |
|   | 0.3 | 12 |   |   | 9 |   |   |
|   | 1.0 | 27 |   |   | 15 |   |   |
|   | 3.0 | 58 |   |   | 22 |   |   |
| 2 | 0.1 | 6 | 0.24 | 0.45 | 0 | 0.35 | 0.75 |
|   | 0.3 | 29 |   |   | 18 |   |   |
|   | 1.0 | 88 |   |   | 60 |   |   |
|   | 3.0 | 100 |   |   | 84 |   |   |
| 3 | 0.3 | 25 | 0.3 | 0.45 | 40 | <0.3 | 0.4 |
|   | 1.0 | 98 |   |   | 88 |   |   |
|   | 10.0 | 100 |   |   | 92 |   |   |
| 4 | 0.1 | 1 | 0.24 | 0.55 | +5 | 0.48 | 1.0 |
|   | 0.3 | 30 |   |   | 10 |   |   |
|   | 1.0 | 69 |   |   | 50 |   |   |
|   | 3.0 | 89 |   |   | 75 |   |   |
| 5 | 10.0 | 5 | 16.0 | 30.0 | 0 | — | >100 |
|   | 30.0 | 51 |   |   | 0 |   |   |
|   | 100.0 | 61 |   |   | 15 |   |   |
| 6 | 1.0 | 27 | ~1.0 | 1.4 | 15 | 1.2 | 2.0 |
|   | 3.0 | 97 |   |   | 70 |   |   |
| 7 | 0.3 | 30 | ≲0.3 | 0.5 | 26 | 0.3 | 0.5 |
|   | 1.0 | 94 |   |   | 85 |   |   |

| Serial No. | Dose [mg/kg] p.o. | Protective action on the stomach (rat) | | | Gastric Secretion (rat) | | |
|---|---|---|---|---|---|---|---|
| | | reduction in the ulcer index (%) | ED$_{25}$+ [mg/kg, p.o.] | ED$_{50}$+ | inhibition in % of HCl-secretion | ED$_{25}$+ [mg/kg, p.o.] | ED$_{50}$+ |
| 8 | 1.0 | 50 | <<1.0 | 1.0 | 12 | 1.5 | 3.0 |
| | 3.0 | 63 | | | 50 | | |

+ED$_{25}$ and ED$_{50}$ (logarithmic interpolation) = dose which reduces the ulcer index and the HCl-secretion (Σ 4 hours) of the rat stomach by 25% and 50% in the treated group compared with the control group.

The antiulcerogenic action was tested in accordance with the method using the so-called Shay rat: Rats (female, 180 to 200 g, 4 animals per cage on a high grid) which had been fasted for 24 hours were subjected to ulcer provocation by pylorus ligature (under diethyl ether anaesthesia) and oral administration of 100 mg/10 ml/kg of acetylsalicyclic acid. The substances to be tested are administered orally (10 ml/kg) 1 hour before the pylorus ligature. The wound is closed by means of Michel clamps. 4 hours thereafter, the animals are killed under ether anaesthesia by atlas dislocation, and the stomach is removed. The stomach is opened longitudinally and fixed to a cork tile after the amount of gastric juice secreted [volume, and its hydrochloric acid content (titration with sodium hydroxide solution)] has been determined, the number and size (=diameter) of ulcers present are determined with a stereomicroscope with 10-fold magnification. The product of the degree of severity (according to the following rating scale) and the number of ulcers serves as the individual ulcer index.

Scale of points:

| no ulcers | 0 |
|---|---|
| ulcer diameters | 0.1–1.4 mm 1 |
| | 1.5–2.4 mm 2 |
| | 2.5–3.4 mm 3 |
| | 3.5–4.4 mm 4 |
| | 4.5–5.4 mm 5 |
| | 5.5 mm 6 |

The reduction in the average ulcer index of each treated group compared with that of the control group (=100%) serves as a measure of the antiulcerogenic effect. The ED$_{25}$ and the ED$_{50}$ designate the doses which reduce the average ulcer index and the gastric secretion by 25 and 50%.

TOXICITY

The dosis tolerata of all tested compounds is >1000 mg/kg [p.o.].

The invention and its advantages are readily understood from the preceding description. Various changes may be made in the compounds, in the compositions, in the administration and in the use without departing from the spirit and scope of the invention or sacrificing its material advantages. The described processes, products and uses are merely illustrative of preferred embodiments of the invention.

What is claimed is:

1. A substituted benzimidazole of the formula

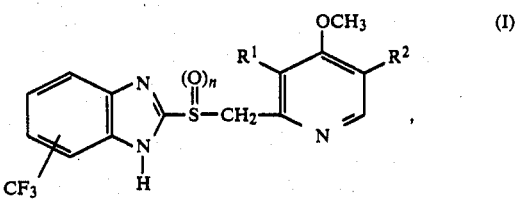

wherein
R$^1$ denotes —H or methyl,
R$^2$ denotes —H or methyl and
n denotes zero or 1,
or a salt thereof.

2. A substituted benzimidazole according to claim 1 of the formula

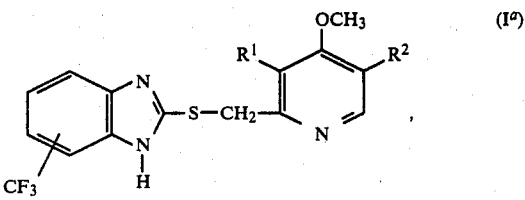

wherein R$^1$ an R$^2$ have their previously-ascribed meanings, or a salt thereof.

3. A substituted benzimidazole according to claim 1 of the formula

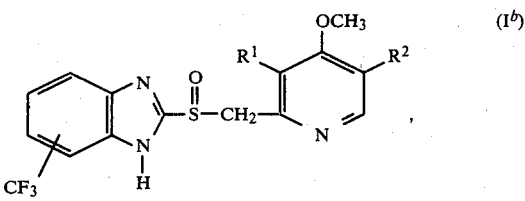

wherein R$^1$ and R$^2$ have their previously-ascribed meanings, or a salt thereof.

4. A compound according to claim 2 selected from the group consisting of 4-trifluoromethyl-2-[(4-methoxy-2-pyridylmethyl)thio]-(1H)-benzimidazole, 4-trifluoromethyl-2-[(4-methoxy-3-methyl-2-pyridylmethyl)thio]-(1H)-benzimidazole, 4-trifluoromethyl-2-[(4-methoxy-5-methyl-2-pyridylmethyl)thio]-(1H)-benzimidazole, 4-trifluoromethyl-2-[(4-methoxy-3,5-dimethyl-2-pyridylmethyl)thio]-(1H)-benzimidazole, 5-trifluoromethyl-2-[(4-methoxy-2-pyridylmethyl)thio]-(1H)-benzimidazole, 5-trifluoromethyl-2-[(4-methoxy-3-methyl-2-pyridylmethyl)thio]-(1H)-benzimidazole, 5-trifluoromethyl-2-[(4-methoxy-5-methyl-2-pyridylmethyl)thio]-(1H)-benzimidazole and 5-trifluoromethyl-2-[(4-methoxy-3,5-dimethyl-2-pyridylmethyl)thio]-(1H)-benzimidazole, a tautomer thereof and a salt of one of these compounds.

5. A compound according to claim 3 selected from the group consisting of 4-trifluoromethyl-2-[(4-methoxy-2-pyridylmethyl)sulfinyl]-(1H)-benzimidazole, 4-trifluoromethyl-2-[(4-methoxy-3-methyl-2-pyridylmethyl)sulfinyl]-(1H)-benzimidazole, 4-trifluoromethyl-2-[(4-methoxy-5-methyl-2-pyridylmethyl)sulfinyl]-(1H)-benzimidazole, 4-trifluoromethyl-2-[(4-methoxy-3,5-dimethyl-2-pyridylmethyl)sulfinyl]-(1H)-benzimidazole, 5-trifluoromethyl-2-[(4-methoxy-2-pyridylmethyl)sulfinyl]-(1H)-benzimidazole, 5-trifluoromethyl-2-[(4-methoxy-3-methyl-2-pyridylmethyl)sulfinyl]-(1H)-benzimidazole, 5-trifluoromethyl-2-[(4-methoxy-5-methyl-2-pyridylmethyl)sulfinyl]-(1H)-benzimidazole and 5-trifluoromethyl-2-[(4-methoxy-3,5-dimethyl-2-pyridylmethyl)sulfinyl]-(1H)-benzimidazole, a tautomer thereof and a salt of one of these compounds.

6. A pharmacologically-acceptable compound which is a substituted benzimidazole according to claim 1 or a salt thereof.

7. A pharmacologically-acceptable compound which is a substituted benzimidazole according to claim 2 or a salt thereof.

8. A pharmacologically-acceptable compound which is a substituted benzimidazole according to claim 3 or a salt thereof.

9. A medicament composition comprising active ingredient and pharmaceutical auxiliary, the active ingredient comprising from 0.1 to 95 percent by weight of at least one pharmacologically-acceptable compound according to claim 6.

10. A method for treatment or prophylaxis of illness based on excessive secretion of hydrochloric acid in the stomach which comprises administering an effective amount of a compound according to claim 6 to a mammal afflicted with or subject to attacks of such illness.

11. A method of providing protective action for the stomach and intestines which comprises administering an effective amount of a compound according to claim 6 to a warm-blooded animal.

12. A medicament composition for protecting the stomach of a warm-blooded animal which comprises pharmaceutical auxiliary and an effective amount of a compound according to claim 6.

13. A medicament composition for treatment or prophylaxis of illness based on excessive secretion of hydrochloric acid in the stomach of a mammal which comprises pharmaceutical auxiliary and an effective amount of a compound according to claim 6.

14. A compound according to claim 1 which is 4-trifluoromethyl-2-[(4-methoxy-2-pyridylmethyl)sulfinyl]-(1H)-benzimidazole or a pharmacologically-acceptable salt thereof.

15. A compound according to claim 1 which is 5-trifluoromethyl-2-[(4-methoxy-2-pyridylmethyl)sulfinyl]-(1H)-benzimidazole or a pharmacologically-acceptable salt thereof.

16. A compound according to claim 1 which is 5-trifluoromethyl-2-[(4-methoxy-3-methyl-2-pyridylmethyl)sulfinyl]-(1H)-benzimidazole or a pharmacologically-acceptable salt thereof.

17. A compound according to claim 1 which is 5-trifluoromethyl-2-[(4-methoxy-3,5-dimethyl-2-pyridylmethyl)sulfinyl]-(1H)-benzimidazole or a pharmacologically-acceptable salt thereof.

18. A compound according to claim 1 which is 5-trifluoromethyl-2-[(4-methoxy-3-methyl-2-pyridylmethyl)thio]-(1H)-benzimidazole or a pharmacologically-acceptable salt thereof.

19. A compound according to claim 1 which is 5-trifluoromethyl-2-[(4-methoxy-2-pyridylmethyl)thio]-(1H)-benzimidazole or a pharmacologically-acceptable salt thereof.

20. A compound according to claim 1 which is 4-trifluoromethyl-2-[(4-methoxy-3-methyl-2-pyridylmethyl)thio]-(1H)-benzimidazole or a pharmacologically-acceptable salt thereof.

21. The compound according to claim 1 which is 5-trifluoromethyl-2-[(4-methoxy-3,5-dimethyl-2-pyridylmethyl)thio]-(1H)-benzimidazole.

22. A substituted benzimidazole according to claim 3 which is in basic-salt form.

23. A substituted benzimidazole according to claim 3 which is 5-trifluoromethyl-2-[(4-methoxy-2-pyridylmethyl)-sulfinyl]-(1H)-benzimidazole sodium salt.

* * * * *